US012268706B2

(12) United States Patent
Müller-Lierheim et al.

(10) Patent No.: US 12,268,706 B2
(45) Date of Patent: Apr. 8, 2025

(54) HYALURONIC ACID FOR RELIEF OF IDIOPATHIC OCULAR PAIN

(71) Applicant: I.COM MEDICAL GMBH, Munich (DE)

(72) Inventors: Wolfgang Georg Konrad Müller-Lierheim, Munich (DE); Gysbert-Botho Van Setten, Danderyd (SE)

(73) Assignee: I.COM MEDICAL GMBH, Munich (DE)

( * ) Notice: Subject to any disclaimer, the term of this patent is extended or adjusted under 35 U.S.C. 154(b) by 856 days.

(21) Appl. No.: 17/309,463

(22) PCT Filed: Jan. 31, 2020

(86) PCT No.: PCT/IB2020/000053
§ 371 (c)(1),
(2) Date: May 28, 2021

(87) PCT Pub. No.: WO2020/157570
PCT Pub. Date: Aug. 6, 2020

(65) Prior Publication Data
US 2021/0369764 A1 Dec. 2, 2021

Related U.S. Application Data

(60) Provisional application No. 62/799,245, filed on Jan. 31, 2019.

(51) Int. Cl.
*A61K 31/728* (2006.01)
*A61K 9/00* (2006.01)
(52) U.S. Cl.
CPC .......... *A61K 31/728* (2013.01); *A61K 9/0048* (2013.01)
(58) Field of Classification Search
CPC .............................. A61K 31/728; A61K 9/0048
See application file for complete search history.

(56) References Cited

U.S. PATENT DOCUMENTS

| | | | |
|---|---|---|---|
| 6,107,347 | A | 8/2000 | Francese et al. |
| 8,680,078 | B2 | 3/2014 | Aleo et al. |
| 8,853,150 | B2 | 10/2014 | Barnes et al. |
| 2005/0043271 | A1 | 2/2005 | Gross et al. |
| 2005/0164979 | A1 | 7/2005 | Gross et al. |
| 2009/0111770 | A1 | 4/2009 | Holzer et al. |
| 2012/0122976 | A1 | 5/2012 | Holzer |
| 2014/0221309 | A1 | 8/2014 | Beard et al. |
| 2014/0228364 | A1 | 8/2014 | Hadj-Slimane |
| 2016/0193234 | A1 | 7/2016 | Joo et al. |
| 2017/0014339 | A1 | 1/2017 | Mueller-Lierheim |
| 2017/0071875 | A1 | 3/2017 | Martinez et al. |
| 2017/0071974 | A1 | 3/2017 | Balazs et al. |
| 2021/0077523 | A1 | 3/2021 | Müller-Lierheim et al. |
| 2021/0145862 | A1 | 5/2021 | Müller-Lierheim et al. |
| 2023/0233687 | A1 | 7/2023 | Müller-Lierheim |
| 2023/0241096 | A1 | 8/2023 | Müller-Lierheim et al. |
| 2023/0338541 | A1 | 10/2023 | Müller-Lierheim |

FOREIGN PATENT DOCUMENTS

| | | |
|---|---|---|
| CN | 104666139 A1 | 6/2015 |
| DE | 103 60 425 | 7/2005 |
| DE | 102005055275 A1 | 5/2007 |
| DE | 102009008940 A1 | 8/2010 |
| EP | 2070518 A2 | 6/2009 |
| EP | 2316420 A1 | 5/2011 |
| EP | 2543357 A1 | 1/2013 |
| EP | 3056195 A1 | 8/2016 |
| JP | 2005-513106 A | 5/2005 |
| JP | 2013-535204 A | 9/2013 |
| JP | 2016-65089 A | 4/2016 |
| KR | 10-2009-0053892 A | 5/2009 |
| KR | 10-2012-0047851 A | 5/2012 |
| TW | 201945010 A | 12/2019 |
| WO | WO-94/09795 | 5/1994 |
| WO | WO 00/08061 A1 | 2/2000 |
| WO | WO-03/049747 | 6/2003 |
| WO | WO-03/053453 | 7/2003 |
| WO | WO-2008/072905 | 6/2008 |
| WO | WO-2008/126803 | 10/2008 |
| WO | WO-2009/025763 | 2/2009 |
| WO | WO-2012/119261 | 3/2012 |
| WO | WO-2016/089807 | 6/2016 |
| WO | WO 2017/012712 | 1/2017 |
| WO | WO-2017/053339 | 3/2017 |
| WO | WO-2018/069763 | 4/2018 |

(Continued)

OTHER PUBLICATIONS

Jacobs, D.S., Curr. Ophthalmol. Rep., 2017, 5, p. 271-275. (Year: 2017).*
Gomis et al., Arthritis & Rheumatism, 2004, 50(1), p. 314-326. (Year: 2004).*
Definition of analogue, Oxford English Dictionary, https://www.oed.com/, accessed online on May 28, 2024. (Year: 2024).*
Anonymous, "A Brief Conversion Relationship Between Intrinsic Viscosity and Molecular Weight—Freshinechem", Jul. 5, 2018, pp. 1-2, Retrieved from the Internet: URL: https://www.freshinechem.com/a-brief-conversion-relationship-between-intrinsic-viscosity-and-molecular-weight/.
"ICD-10 Coding for Dry Eye", 2015, pp. 1-2.

(Continued)

*Primary Examiner* — Jonathan S Lau
(74) *Attorney, Agent, or Firm* — SALIWANCHIK, LLOYD & EISENSCHENK

(57) ABSTRACT

The invention concerns a method for relieving idiopathic ocular pain by administering an effective amount of a fluid composition comprising hyaluronic acid, a hyaluronic acid analogue, or a combination thereof, to the eye of a human or non-human animal subject, wherein the fluid composition is administered after onset of the idiopathic ocular pain and in the absence of detectable signs known to cause ocular pain.

16 Claims, No Drawings

(56) References Cited

FOREIGN PATENT DOCUMENTS

| | | |
|---|---|---|
| WO | WO-2019/202015 | 10/2019 |
| WO | WO-2019/202017 | 10/2019 |
| WO | WO-2021/250462 | 12/2021 |
| WO | WO-2021/260427 | 12/2021 |
| WO | WO-2021/260430 | 12/2021 |

OTHER PUBLICATIONS

Radda, T. M. et al. "Trockenes Auge—Therapie mit hypoosmolaren Natrium-Hyaluronat-Tropfen" *Spektrum der Augenheilkunde*, 1989, pp. 174-176, vol. 3/4 (includes machine translation).
U.S. Appl. No. 62/516,911, filed Jun. 8, 2017, pp. 1-42.
U.S. Appl. No. 62/408,559, filed Oct. 14, 2016, pp. 1-34.
Guidelines from BVA (Professional Association of Ophthalmologists) and DOG (German Ophthalmological Society) on dry eye (2019) (includes machine translation).
Schiffman et al. "Reliability and validity of the ocular surface index" *Arch Ophthalmology*, 2000, 118:615-621.
Miller et al. "Minimally Clinically Important Difference for the Ocular Surface Disease Index" *Arch Ophthalmology*, 2010, 128:94-101.
Ursapharm Product Catalogue from website, printed Feb. 2023.
Ocular Surface Disease Index (OSDI) questionnaire, 1995.
Leith et al. "Comparison of the properties of AMCISC® and Healon®" *Journal of Cataract & Refractive Surgery*, 1987, 13(5):534-6.
Hylo®-Gel Brochure—URSAPHARM.
Annotated Ursapharm viscosity chart including positions for Applicant products.
Aragona et al. "Physicochemical Properties of Hyaluronic Acid-Based Lubricant Eye Drops" *Translational vision science and technology*, 2019, 8(6):1-11.
Notice of Opposition, dated Nov. 10, 2022, European Appl. No. 17817868.7.
Applicant response to opposition, dated Mar. 20, 2023, European Appl. No. 17817868.7.
Al-Assaf, S. et al. "Molecular interaction studies of the hyaluronan derivative, hylan A using atomic force microscopy" *Carbohydrate Polymers*, 2002, pp. 341-345, vol. 47.
Aragona, P. et al. "Modern approach to the treatment of dry eye, a complex multifactorial disease: a P.I.C.A.S.S.O. board review" Br J Ophthalmol, Apr. 2021 (Epub Jul. 2020), 105(4):446-453.
Ardizzoni, A. et al. "Influence of hyaluronic acid on bacterial and fungal species, including clinically relevant opportunistic pathogens" *J Mater Sei: Mater Med*, 2011, pp. 2329-2338, vol. 22.
Baenninger, P. B. et al. "Variability of Tear Osmolarity Measurements With a Point-of-Care System in Healthy Subjects-Systematic Review" *Cornea*, Jul. 2018, pp. 938-945, vol. 37, No. 7.
Balazs, E. A. and Leshchiner, E. A. "Hyaluronan, its cross-linked derivative—hylan—and their medical applications" *Cellulosics Utilization: Research and Rewards in Cellulosics, Proceedings of Nisshinbo International Conference on Cellulosics Utilization in the Near Future*, Elsevier Applied Science, NY, 1989, pp. 233-241.
Baudouin, C. "A new approach for better comprehension of diseases of the ocular surface" *J. Fr. Ophtalmol.*, 2007, 30(3):239-246; abstract.
Baudouin, C. et al. "Clinical impact of inflammation in dry eye disease: proceedings of the ODISSEY group meeting" *Acta Ophthalmologica*, 2017, pp. 1-9.
Baudouin, C. et al. "Diagnosing the severity of dry eye: a clear and practical algorithm" *Br J Ophthalmol*, 2014, pp. 1168-1176, vol. 98.
Beck, R. et al. "Hyaluronic Acid as an Alternative to Autologous Human Serum Eye Drops: Initial Clinical Results with High-Molecular-Weight Hyaluronic Acid Eye Drops" *Case Rep Ophthalmol*, 2019, pp. 244-255, vol. 10.
Belmonte, C. et al. "TFOS DEWS II pain and sensation report" *The Ocular Surface*, 2017, pp. 404-437, vol. 15, No. 3.

Benz, M. et al. "Lubrication and wear properties of grafted polyelectrolytes, hyaluronan and hylan, measured in the surface forces apparatus" *J. Biomed. Mater. Res.*, Oct. 2004, pp. 6-15, vol. 71A.
Berry, G.C. and Fox, T.G. "The Viscosity of Polymers and their Concentrated Solutions" *Adv. Polymer Sci.*, 1968, 5:261-357.
Bron, A. et al. "TFOS DEWS II pathophysiology report" *The Ocular Surface*, 2017, 15:438-510.
Caires, R. et al. "Hyaluronan modulates TRPV1 channel opening, reducing peripheral nociceptor activity and pain" *Nature Communications*, 2015, pp. 1-11, vol. 6, No. 8095.
Calciu-Rusu, D. et al. "Rheology of Sodium Hyaluronate Saline Solutions for Ophthalmic Use" *Biomacromolecules*, 2007, 8:1287-1292.
Camillieri, G. et al. "Hyaluronan-Induced Stimulation of Corneal Wound Healing is a Pure Pharmacological Effect" *J. Ocular Pharmacology & Therapeutics*, 2004, 20(6):548-553.
Cermelli, C. et al. "In vitro evaluation of antiviral and virucidal activity of a high molecular weight hyaluronic acid" *Virology Journal*, 2011, pp. 1-8, vol. 8, No. 141.
Code of Federal Regulations, Part 349—Ophthalmic Drug Products for Over-the-Counter Human Use, Nov. 14, 2019 (7 pages).
Comfort Shield® SD brochure. Copyright Nov. 2015; Manufacturer: i.com medical GmbH.
Condon, P. et al. "Double blind, randomised, placebo controlled, crossover, multicentre study to determine the efficacy of a 0.1% (w/v) sodium hyaluronate solution (Fermavisc) in the treatment of dry eye syndrome" *Br. J. Ophthalmol.*, 1999, 83:1121-1124.
Costagliola, C. et al. "The ability of bacteria to use Na-hyaluronate as a nutrient" *Acta Ophthalmol. Scand.*, 1996, pp. 566-568, vol. 74.
Cowman, M. K. et al. "Tapping mode atomic force microscopy of the hyaluronan derivative, hylan A" *Carbohydrate Polymers*, 2000, pp. 229-235, vol. 41.
Craig, J. P. et al. "TFOS DEWS II Definition and Classification Report" *The Ocular Surface*, 2017, pp. 276-283, vol. 15, No. 3.
Cyphert, J. M. et al. "Size Matters: Molecular Weight Specificity of Hyaluronan Effects in Cell Biology" *International Journal of Cell Biology*, 2015, pp. 1-8.
Dick, H.B. et al. "Osmolality of various viscoelastic substances: Comparative study" *J. Cataract. Refract. Surg.*, 2000, 26:1242-1246.
Foulks, G.N. (Editor-in-Chief), "2007 Report of the International Dry Eye WorkShop (DEWS)" *The Ocular Surface*, Apr. 2007, vol. 5, No. 2 (142 pages).
Galor, A. et al. "Incomplete response to artificial tears is associated with features of neuropathic ocular pain" *Br. J. Ophthalmol.*, 2016, 100:745-749.
Gomis, A et al. "Effects of Different Molecular Weight Elastoviscous Hyaluronan Solutions on Articular Nociceptive Afferents" *Arthritis & Rheumatism*, Jan. 2004, pp. 314-326, vol. 50, No. 1.
Gomis, A. et al. "Intra-articular injections of hyaluronan solutions of different elastoviscosity reduce nociceptive nerve activity in a model of osteoarthritic knee joint of the guinea pig" *Osteoarthritis and Cartilage*, 2009, pp. 798-804, vol. 17, No. 6.
Goyal, S. and Hamrah, P. "Understanding Neuropathic Corneal Pain-Gaps and Current Therapeutic Approaches" *Semin Ophthalmol.*, 2016, 31(1-2):59-70.
Graessley, W. "The Entanglement Concept in Polymer Rheology" *Adv. Polymer Sci.*, 1974, pp. 1-179.
Gross, D. et al. "Comparison of 0.2% and 0.18% hyaluronate eye drops in patients with moderate to severe dry eye with keratitis or keratoconjunctivitis" *Clinical Ophthalmology*, 2017, 11:631-638.
Higashide, T. et al. "Use of viscoelastic substance in ophthalmic surgery—focus on sodium hyaluronate" *Clinical Ophthalmology*, 2008, pp. 21-30, vol. 2, No. 1.
HYLAFORM® (hylan B gel) Explained, patient labeling, Jul. 28, 2004, 10 pages.
Hylan A-10, Material Safety Data Sheet, Genzyme No. 7440-001, printed Mar. 16, 2005, pp. 1-6.
Jacobs, D. "Diagnosis and Treatment of Ocular Pain: the Ophthalmologist's Perspective" *Curr Ophthalmol Rep*, 2017, 5(4):271-275.
Japanese Pharmacopoeia JP XVII "Purified Sodium Hyaluronate Ophthalmic Solution" 2016, pp. 1577-1578.

(56) References Cited

OTHER PUBLICATIONS

Japanese Pharmacopoeia JP XVII "Purified Sodium Hyaluronate" 2016, pp. 1575-1576.
Jiang, D. et al. "Hyaluronan as an Immune Regulator in Human Diseases" *Physiol Rev*, 2011, 91:221-264.
Jones, L. et al. "TFOS DEWS II Management and Therapy Report" *The Ocular Surface*, 2017, pp. 575-628, vol. 15.
Kalluri, R. et al. "The basics of epithelial-mesenchymal transition" *The Journal of Clinical Investigation*, Jun. 2009, vol. 119, No. 6.
Kent, C. "Dry-Eye Guidelines: Making a Difference in the Clinic?" *Review of Ophthalmology*, Oct. 2008 (9 pages).
Knop, E. et al. "Anatomy and immunology of the ocular surface" *Chem Immunol Allergy*, 2007, pp. 36-49, vol. 92.
Koehler, L. et al. "Sulfated Hyaluronan Derivatives Modulate TGF-β1:Receptor Complex Formation: Possible Consequences for TGF-β1 Signaling" *Scientific Reports*, 2017, pp. 1-11, vol. 7, No. 1210.
Kojima, T. et al. "Autologous Serum Eye Drops for the Treatment of Dry Eye Diseases" *Cornea*, Sep. 2008, pp. S25-S30, vol. 27, No. 8, Suppl. 1.
Kojima, T. et al. "The Effects of High Molecular Weight Hyaluronic Acid Eye Drop Application in Environmental Dry Eye Stress Model Mice" *Int. J. Mol. Sci.*, 2020, pp. 1-15, vol. 21.
Krzoska, A. and Moest, P. "Effectiveness of Comfort Shield MDS—Results of a Clincal Investigation at Beuth Hochschule fur technik Berlin" *Galifa Augenblick*, Jul. 2016, pp. 1-8, in German, with English translation.
Kymionis, G. D et al. "Treatment of chronic dry eye: focus on cyclosporine" *Clinical Ophthalmology*, 2008, pp. 829-836, vol. 2, No. 4.
Lee, D. G. et al. "Preventive Effects of Hyaluronic Acid on *Escherichia coli*-induced Urinary Tract Infection in Rat" *Urology*, 2010, vol. 75, No. 4.
Liu, X. et al. "Therapeutic Effects of Sodium Hyaluronate on Ocular Surface Damage Induced by Benzalkonium Chloride Preserved Anti-glaucoma Medications" *Chin. Med. J.*, 2015, 128:2444-2449.
Löw, M. et al. "Vergleich von Healon®, Healon®GV und Healon®5 bei der Viskotrabekulektomie" *Ophthalmologe*, 2003, 100(7):539-544 (includes online machine translation). [LOW].
Lu, Q. et al. "An In Vitro Model for the Ocular Surface and Tear Film System" *Scientific Reports*, 2017, pp. 1-11, vol. 7, No. 6163.
Mazzacane, D. and Braggio, F. "Randomized controlled trial of high-molecular-weight hyaluronic acid in dry eye sindromes" *Ann. Di Oftalmo. e Clin. Oculist.*, 1993, 115:1-15.
Mehra, D. et al. "Ocular Surface Pain: A Narrative Review" *Ophthalmol Ther*, 2020, 9(3):1-21.
Messmer, E. M. "The Pathophysiology, Diagnosis, and Treatment of Dry Eye Disease" *Dtsch Arztebl Int*, 2015, pp. 71-82.
Mueller-Lierheim, W.G.K. "Guidelines. Tear substitute and contact rewetting solutions" *Aktkontaktol*, Apr. 2015, Issue 11, No. 24, pp. 8-15.
Mueller-Lierheim, W.G.K. "Why Chain Length of Hyaluronan in Eye Drops Matters" *Diagnostics*, 2020, 10:511 (32 pages).
Mueller-Lierheim, W.G.K. "New aspects of the use of hyaluronic acid on the ocular surface", presented at the annual meeting of the Romanian Contact Lens Society and Romanian Society of Cornea and Ocular Surface, Sibiu, Romania, Nov. 4-5, 2016, Poster and Abstract.
Mueller-Lierheim, W.G.K. "Tear substitutes. Latest information on hyaluronic acid" *Aktkontaktol*, Apr. 2015, Issue 11, No. 24, pp. 17-19.
Mueller-Lierheim, W.G.K. "The HYLAN M Study. Study design and first results" *Aktkontaktol*, Jan. 2017, Issue 13, No. 27 (3 pages).
Nakamura, M. et al. "Concentration and molecular weight dependency of rabbit corneal epithelial wound healing on hyaluronan" *Curr Eye Res*, 1992, 11(10):981-986.
Necas, J. et al. "Hyaluronic acid (hyaluronan): a review" *Veterinarni Medicina*, 2008, pp. 397-411, vol. 8.
Noble, P. W. "Hyaluronan and its catabolic products in tissue injury and repair" *Matrix Biol.*, Jan. 2002, pp. 25-29, vol. 21, No. 1.

Patel, S. et al. "Corneal Nerve Abnormalities in Ocular and Systemic Diseases" *Exp Eye Res*, 2021, 202:108284 (18 pages).
Pattmoeller, M. et al. "Safety of Hyaluronic Acid in Postoperative Treatment after Penetrating Keratoplasty" *Klin Monatsbl Augenheilkd*, 2018, 235:64-72.
Pavan, M. et al. "Hyaluronan derivatives: Alkyl chain length boosts viscoelastic behavior to depolymerization" *Carbohydrate Polymers*, 2013, pp. 321-326, vol. 97, No. 2.
Pena, E. et al. "TRPV1 channel modulation by hyaluronan reduces pain" *Channels*, 2016, pp. 81-82, vol. 10, No. 2.
Pflugfelder, S. C. et al. "Epithelial-Immune Cell Interaction in Dry Eye" *Cornea*, Sep. 2008, pp. 1-7.
Polack, F.M. and Mcniece, M.T. "The Treatment of Dry Eyes with Na Hyaluronate (Healon®)" *Cornea*, Jun. 1982, pp. 133-136, vol. 1, No. 2.
Rah, M. J. "A review of hyaluronan and its ophthalmic applications" *Optometry*, 2011, pp. 38-43, vol. 82.
Rea, M. S. and Ouellette, M. J. "Relative visual performance. A basis for application" *Lightning Res. Technol.*, 1991, pp. 135-144, vol. 23, No. 3.
Salzillo, R. et al. "Optimization of hyaluronan-based eye drop formulations" *Carbohydrate Polymers*, 2016, pp. 275-283, vol. 153.
Schrager, H. M. et al. "Hyaluronic Acid Capsule and the Role of Streptococcal Entry into Keratinocytes in Invasive Skin Infection" Nov. 1996, pp. 1954-1958, vol. 98, No. 9.
Schultz, C. "Safety and Efficacy of Cyclosporine in the Treatment of Chronic Dry Eye" *Ophthalmology and Eye Diseases*, 2014, pp. 37-42, vol. 6.
Schulz, K. et al. "CONSORT 2010 Statement: Updated guidelines for reporting parallel group randomised trials" *J. Clin. Epidemiology*, 2010, pp. 1-7.
Shaheen, B. et al. "Corneal Nerves in Health and Disease" *Surv Ophthalmol.*, 2014, 59(3):263-285.
Shimmura, S. et al. "Sodium hyaluronate eyedrops in the treatment of dry eyes" *Br. J. Ophthalmology*, 1995, 79:1007-1011.
Shiseido, Certificate of Analysis, "Shiseido Sodium Hyaluronate SZE Grade •EP" Mar. 31, 2015.
Shiseido, Certificate of Suitability No. R1-CEP 2010-113-Rev 00, "Sodium Hyaluronate" Sep. 16, 2016.
Simsek, C. et al. "Alterations of Murine Subbasal Corneal Nerves After Environmental Dry Eye Stress" *IOVS*, Apr. 2018, pp. 1986-1995, No. 5, vol. 59.
Sodium hyaluronate, European Pharmacopoeia (Ph. Eur.) 9th Edition, Jan. 2017, pp. 3583-3585.
Stern, R. et al. "Hyaluronan fragments: An information-rich system" *European Journal of Cell Biology*, 2006, pp. 699-715, vol. 85.
Sullivan, B. D. et al. "An Objective Approach to Dry Eye Disease Severity" *Investigative Ophthalmology & Visual Science*, Dec. 2010, pp. 6125-6130, vol. 51, No. 12.
Sullivan, B.D. "Response to 'Variability of Tear Osmolarity Measurements With a Point-of-Care System in Healthy Subjects-Systematic Review" *Cornea*, Jun. 2019, pp. e21-e23, vol. 38, No. 6.
Takigami, S. et al. "Hydration characteristics of the cross-linked hyaluronan derivative hylan" *Carbohydrate Polymers*, 1993, pp. 153-160, vol. 22.
Third party observation filed in related European Patent Application No. 17817868.7 on Dec. 11, 2020; in German with English translation.
Toda, I. et al. "Visual Performance After Reduced Blinking in Eyes With Soft Contact Lenses or After LASIK" *Journal of Refractive Surgery*, Jan. 2009, pp. 69-73, vol. 25.
Tsubota, K. et al. "A New Perspective on Dry Eye Classification: Proposal by the Asia Dry Eye Society" *Eye & Contact Lens*, 2020, 46(Supplement 1):S2-S13.
Tsubota, K. et al. "New Perspectives on Dry Eye Definition and Diagnosis: A Consensus Report by the Asia Dry Eye Society" *The Ocular Surface*, 2017, 15(1):65-76.
Van Setten et al. "High Molecular Weight Hyaluronan Promotes Corneal Nerve Growth in Severe Dry Eyes" *J. Clin. Med.*, 2020, 9:3799 (13 pages).

(56) References Cited

OTHER PUBLICATIONS

Van Setten, G. "Sandbank Epitheliopathy of the Conjunctiva (SEC) s New Indicator in Dry Eye Diagnostics Useful for Optimized Ocular Surgery" *Journal of Eye & Cataract Surgery*, 2017, pp. 1-4, vol. 3, No. 2:29.

Van Setten, G. "The Anatomical Dry Eye—A Different Form of Ocular Surface Disease Deserves Focus" *Open Journal of Ophthalmology*, Jul. 17, 2017, pp. 184-190, vol. 7.

Van Setten, G. B. "Osmokinetics: A new dynamic concept in dry eye disease" *Journal français d'ophtalmologie*, 2019, pp. 221-225, vol. 42.

Van Setten, G. et al. "Hyaluronic acid as an alternative to autologous human serum eye drops—initial clinical results with high molecular weight HA", Presented at the ESCRS Congress, Vienna, Switzerland, Sep. 16, 2018.

Van Setten, G-B. et al. "The Hylan M Study: Efficacy of 0.15% High Molecular Weight Hyaluronan Fluid in the Treatment of Severe Dry Eye Disease in a Multicenter Randomized Trial" *J. Clin. Med.*, 2020, 9:3536 (25 pages).

White, C. et al. "Bringing comfort to the masses: A novel evaluation of comfort agent solution properties" *Contact Lens & Anterior Eye*, 2014, 37:81-91.

Wright, M. "Hylan Passes Initial Test for TX of Dry Eye" *Ophthalmology Times*, Oct. 1, 1993, p. 8.

Wu, C-L. et al. "Hyaluronic acid-dependent protection against alkali-burned human corneal cells" *Electrophoresis*, 2013, 34:388-396.

Duygu, G. et al. "The effects of high molecular weight hyaluronic acid (Hylan G-F 20) on experimentally induced temporomandibular joint osteoartrosis: part II" *Int. J. Oral Maxillofac. Surg.*, 2011, 40:1406-1413.

Mueller-Lierheim, W.G.K. "Hyaluronic acid eye drops. What you should know about their rheological properties" *Aktkontaktol*, Dec. 2015, Issue 11, No. 25, pp. 1-3.

Gregory, D. "New grading system and treatment guidelines for the acute ocular manifestations of Stevens-Johnson syndrome" *Ophthalmology*, 2016, 123:1653-1658.

Ramappa, M. et al. "Congenital corneal anesthesia" *J. AAPOS*, 2014, 18:427-432.

Pistorius, A. et al. "The clinical application of hyaluronic acid in gingivitis therapy" *Quintessence Int.*, 2005, 36:531-538.

Romero-Jimenez, M. et al. "Keratoconus: A review" *Contact Lens Anter. Eye*, 2010, 33:157-166.

i.com medical, Munich, Facebook, Mar. 26, 2015, URL: www.facebook.com/icommedical.

Facebook, i.com medical, Mar. 26, 2015, URL: www.facebook.com/photo/?fbid=1556781561248541&set=pcb.1556781727915191.

Brief Communication, Opposition, dated Oct. 17, 2023, European Appl. No. 17817868.7.

Package insert of Hylo Fresh.

Package insert of Hylo Comod.

Package insert of Hylo Gel.

Davis, S. "Topical treatment options for allergic conjunctivitis" South African Family Practice, 2015, 57(4):10-15.

Akpek, E. et al. "A randomized trial of topical cyclosporin 0.05% in topical steroid-resistant atopic keratoconjunctivitis" Ophthalmology, 2004, 111:476-482.

Liao, Y-H. et al. "Hyaluronan: Pharmaceutical Characterization and Drug Delivery" *Drug Delivery*, 2005, 12:327-342.

Albano, G. et al. "Effect of High, Medium, and Low Molecular Weight Hyaluronan on Inflammation and Oxidative Stress in an In Vitro Model of Human Nasal Epithelial Cells" *Mediators of Inflammation*, 2016, pp. 1-13.

Downie, L. and Keller, P. "A Pragmatic Approach to the Management of Dry Eye Disease: Evidence into Practice" *Optometry and Vision Science*, 2015, 92(9):1-10.

Jain, R. et al. "Stevens-Johnson syndrome: The role of an ophthalmologist" *Survey of Ophthalmology*, 2016, 61:396-399.

\* cited by examiner

HYALURONIC ACID FOR RELIEF OF IDIOPATHIC OCULAR PAIN

CROSS-REFERENCE TO RELATED APPLICATIONS

The present application is the National Stage of International Application Number PCT/IB2020/000053, filed Jan. 31, 2020, which claims the benefit of U.S. Provisional Application Ser. No. 62/799,245, filed Jan. 31, 2019, which is hereby incorporated by reference herein in its entirety, including any figures, tables, nucleic acid sequences, amino acid sequences, or drawings.

FIELD OF THE INVENTION

The present invention concerns a fluid for alleviating ocular pain of unknown etiology.

BACKGROUND OF THE INVENTION

Eye pain (also called ocular pain or ophthalmalgia) involves sensory-discriminative, emotional, cognitive, and behavioral components. Normal or physiological pain results from the stimulation of sensory axons of neurons enervating the eye. These neurons are functionally heterogeneous, having distinct sensitivities to stimulating forces determined by the expression of specific classes of ion channels, including Piezo2 for mechanical forces, TRPV1 and TRPA1 for heat and chemical agents, and TRPM8 for cold stimuli (Belmonte C et at, "What Causes Eye Pain", *Curr Ophthalmol Rep,* 2015, 3:111-121). The types of receptors that predominate in sensations associated with ocular pain vary with the type of stimuli, acute or chronic nature of the condition, the extent of inflammation, etc. Some examples of conditions that cause ocular pain are infection, inflammation, contact lens problem, dry eye, acute glaucoma, sinus problem, eyestrain, headache, and flu.

The cornea has a much greater concentration of nerve endings and pain receptors than elsewhere in the human body, even more so than sensitive areas such as the skin and dental pulp (Carlos Belmonte, EuCornea Medal Lecture, "Neural basis of eye surface sensations. From dryness to pain", Vienna, Sep. 21, 2018). People with ocular pain typically present or are referred to health care providers for evaluation. When there is recent trauma or surgery, or signs of an infectious or inflammatory process, treatment of the underlying process or pathologic abnormality usually results in resolution of the pain. These situations represent physiologic or nociceptive pain (Jacobs D S, "Diagnosis and Treatment of Ocular Pain", *Curr Ophthalmol Rep,* 2017, 5:271-275). Where there are any signs of ocular surface disease (OSD), triaging questions are posed to the patient, and a differential diagnosis between ocular surface diseases is made, and treatment of the differentially diagnosed OSD is administered. Pain associated with surgery, injury, infection, or inflammation at the front of the eye is typically treated with topical steroid, topical non-steroidal anti-inflammatory drug (NSAID), systemic NSAID, lubricant ointment, gel or drops, bandage contact lens, or a few doses of oral opiate or topical anesthetic. When the patient complains of symptoms out of proportion to clinical signs or with no apparent previous insult (no signs or symptoms of ocular surface disease), the presentation is typically characterized as neuropathic pain (absence of ocular surface disease), and is referred for pain management (Craig J P et al., "TFOS DEWS II Definition and Classification Report", *Ocul Surf,* 2017, July, 15(3):276-283).

Since the pain is not nociceptive/pathologic, there is rarely a single treatment that eliminates the pain entirely. For problematic ocular pain, multimodal treatment is recommended, including local, systemic, and cognitive-behavioral approaches (Jacobs D S, 2017). Unfortunately, both the clinicians and patients come to realize that there is currently no effective therapy for the pain perceived.

BRIEF SUMMARY OF THE INVENTION

The inventors provide, for the first time, a treatment for idiopathic ocular pain. The present invention provides a fluid composition and method for alleviating idiopathic ocular pain in a human or non-human animal subject. By administering a fluid composition containing hyaluronic acid (also called hyaluronan or HA), an HA analogue, or both, to the eye, the invention can alleviate (partially reduce or fully eliminate) ocular pain in a subject.

In some embodiments, the HA or HA analogue of the fluid composition is a high molecular weight form of HA and/or high molecular weight HA analogue, e.g., having a molecular weight of 3 million-4 million Daltons, or more. In some embodiments, the high molecular weight form of HA and/or high molecular weight HA analogue has an intrinsic viscosity of >2.5 m$^3$/kg and a concentration of <0.2% w/v. In some embodiments, the intrinsic viscosity is >2.9 m$^3$/kg.

DETAILED DESCRIPTION OF THE INVENTION

Hyaluronic acid (HA) is a carbohydrate—a mucopolysaccharide, specifically, which can be found in living organisms. The biological functions of endogenous HA include maintenance of the elastoviscosity of liquid connective tissues such as joint synovial fluid and eye vitreous fluid (Necas J et al., "Hyaluronic acid (hyaluronan): a review", *Veterinarni Medicina,* 2008, 53(8):397-411; Stern R et al., "Hyaluronan fragments: An information-rich system", *European Journal of Cell Biology,* 2006, 85:699-715). Although the specific mechanisms involved in the diverse signaling of HA are still poorly understood, it is known that HA can modulate multi-faceted biological effects that can vary depending on HA size (Cyphert J M et al., "Size Matters: Molecular Weight Specificity of Hyaluronan Effects in Cell Biology," *International Journal of Cell Biology,* 2015, Epub 2015 Sep. 10, 563818).

Sodium hyaluronate and other viscoelastic agents have been used in intraocular surgery since the 1970s and for treatment of dry eyes since the 1980s (Higashide T and K Sugiyama, "Use of viscoelastic substance in ophthalmic surgery-focus on sodium hyaluronate," *Clinical Ophthalmology,* 2008, 2(1):21-30; Polack F M and M T McNiece, "The treatment of dry eyes with Na hyaluronate (Healon)—preliminary report, 1982, 1(2):133-136); however, little attention has been paid thus far to the biological function of hyaluronic acid in epithelia (Müller-Lierheim W G K, "Tränenersatzlösungen, Neues über Hyaluronsäure," *Aktuelle Kontaktologie,* April 2015, 17-19).

An aspect of the invention includes a method for relieving idiopathic ocular pain, comprising administering an effective amount of a fluid comprising HA, an HA analog, or a combination thereof, to the eye of a human or non-human animal subject, wherein the fluid is administered after onset of the idiopathic ocular pain and in the absence of detectable signs known to cause ocular pain. In addition to reflex responses to ocular pain, such as tearing and blinking, pain sensations have recently been recognized as a primary trigger of secondary physiological effects reflected in undesirable hormonal, metabolic, and cardiorespiratory changes. A prolonged pain-induced stress response may perpetuate cortisol dysfunction and body-wide inflammation. By relieving idiopathic ocular pain, the invention can alleviate and attenuate the secondary cascade of undesirable physiological effects that would otherwise follow.

Without being limited by theory or proposed mechanism of action for idiopathic pain relief, the inventors propose that when a fluid composition comprising HA and/or HA analogue is administered to the eye, the HA or HA analogue molecules may: specifically bind or otherwise directly or indirectly interact with pain receptor proteins within the ocular surface, thereby modulating channel gating, or interfere with access of noxious agents or environmental triggers to the pain receptor proteins, or a combination of such mechanisms of action, resulting in inhibition of pain receptor activity (e.g., reduced responsiveness to noxious stimuli). For example, the HA or HA analogue may directly or indirectly impede conformational changes of the channel needed for opening, locking the channel in the closed state. Accordingly, through its inhibitory action on pain receptor channels in the ocular surface, the HA and/or HA analogue can relieve (alleviate or eliminate) idiopathic ocular pain.

Alternatively, or in addition to the aforementioned modes of action, the HA and/or HA analogue may compensate for fluctuations in tear fluid osmolarity that contribute to eye irritation. Fluctuations in osmolarity can contribute to severity of ocular pain (Kalangara J P et al., "Characteristics of Ocular Pain Complaints in Patients With Idiopathic Dry Eye Symptoms", *Eye Contact Lens*, 2017 May, 43(3): 192-198). An important physiological feature of the osmotic properties of HA is the ability of the constituent polysaccharides to disproportionately increase in osmotic pressure as a function of concentration (pgs. 277-278 of Comper W D and T C Laurent, "Physiologic Function of Connective Tissue Polysaccharides", *Physiol Rev.*, 1978 January, 58(1):255-315). This tends to attenuate the osmotic forces contributing to a disturbance of physiologic homeostasis. Thus, the HA and/or HA analogue may act as an osmolarity buffer, compensating for tear osmolarity fluctuations that would otherwise contribute to irritation and discomfort of the eye.

In some embodiments, the HA and/or HA analogue is high molecular weight, having an intrinsic viscosity of greater than 2.5 m$^3$/kg, and a concentration of <0.2% w/v. In some embodiments, the HA and/or HA analogue is high molecular weight, having an intrinsic viscosity of greater than 2.5 m$^3$/kg, and having a concentration of 0.10 to 0.19% w/v. The intrinsic viscosity may be determined by the method of the European Pharmacopoeia 9.0, "Sodium Hyaluronate", page 3584 (which is incorporated herein by reference in its entirety). Briefly, the intrinsic viscosity [η] is calculated by linear least-squares regression analysis using the Martin equation: $\log_{10}(n_r-1/c) = \log_{10}[\eta] + \kappa[\eta]c$. In some embodiments, the hyaluronic acid or analogue has an intrinsic viscosity of greater than 2.9 m$^3$/kg.

In some embodiments, the HA or HA analogue has a molecular weight of at least 3 million Daltons as calculated by the Mark-Houwink equation. In some embodiments, the HA or HA analogue has a molecular weight in the range of 3 million to 4 million Daltons as calculated by the Mark-Houwink equation.

In some embodiments, the high molecular weight HA is hyaluronan. In some embodiments, the high molecular weight HA or HA analogue is cross-linked. In some embodiments, the high molecular weight HA or HA analogue is non-cross-linked. In some embodiments, the high molecular weight HA or HA analogue is linear. In some embodiments, the high molecular weight HA or HA analogue is non-linear. In some embodiments, the high molecular weight HA is a derivative of hyaluronan, such as an ester derivative, amide derivative, or sulfated derivative, or a combination of two or more of the foregoing.

The fluid may be administered to one or both eyes of the subject by any administration method. In some embodiments, the fluid is topically administered to the ocular surface. For example, the fluid may be administered as one or more drops from a device for dispensing eye drops, such as an eye dropper. In other embodiments, the fluid is administered to the eye by intra-ocular application or by injection into ocular tissue.

The fluid may be self-administered or administered by a third party. The dosage administered, as single or multiple doses, to the eye will vary depending upon a variety of factors, including patient conditions and characteristics, extent of ocular pain, concurrent treatments, frequency of treatment and the effect desired. For example, for topical administration, one or more drops (of, for example, about 30 microliters each) may be administered. In some embodiments, drops of the fluid are topically administered to the ocular surface in an amount and frequency as needed to alleviate ocular pain. While topical administration of 1-3 drops, one to about twenty times per day, may be sufficient for mild to moderate ocular pain, more frequent topical administration may be needed for severe ocular pain and/or chronic ocular pain, particularly during the initial phase of treatment, e.g., 1-3 drops every 30 to 60 minutes.

Relief of the idiopathic ocular pain may be immediate or there may be a delay in relief from the time treatment is initiated. The need for administration of the fluid to the eye may be governed by the sensation of ocular pain by the subject, which can change over time (Zouari H G et al., "The Clinical Features of Painful Small-Fibre Neuropathy Suggesting an Origin Linked to a Primary Sjogren's Syndrome", *Pain Pract.*, 2019 Jan. 12, Epub ahead of print). It may be desirable to continue treatment for a time after relief of the idiopathic ocular pain is achieved. The frequency of administration of the fluid to the eye may be increased, decreased, remain constant, or vary as desired. In some embodiments, the frequency of administration to the eye and/or the amounts per dose can be decreased with time, as ocular pain is alleviated. For example, in some cases, after four weeks, the amount administered may be reduced and/or the frequency of administrations each day may be reduced or the frequency of administrations may be reduced to semi-daily.

Optionally, the fluid is administered to the eye in conjunction with a device, such as a soft or rigid contact lens. For example, the fluid may be topically administered before placement of a contact lens on the ocular surface, such that the fluid is entrapped between the contact lens and the ocular surface. This is advantageous because use of the contact lens can increase residence time of the HA and/or HA analogue on the ocular surface, and the fluid may decrease any discomfort associated with use of the contact lens. The contact lens may be any type or category, such as corneoscleral lenses, semi-scleral lenses, miniscleral lenses, and full scleral lenses.

In some embodiments, the idiopathic ocular pain is partially alleviated by administration of an effective amount of the fluid. In other embodiments, the idiopathic ocular pain is eliminated by administration of an effective amount of the fluid.

The subject may be immunocompromised. The subject's immunocompromised condition may have one or more causes, such as a medical treatment (e.g., radiation therapy, chemotherapy or other immunosuppressing treatment), environmental exposure (e.g., radiation exposure), or genetic defect, whether the defect is expressed as a phenotype, or not (i.e., as a genotype only).

Optionally, the method further comprises the step of identifying the subject as having the idiopathic ocular pain, e.g., through examination of the eye of human or non-human animal subject and/or questioning the human subject.

Optionally, the fluid further includes one or more bioactive agents (e.g., a hydrophobic active ingredient). As used herein, the term "bioactive agent" refers to any substance that has an effect on the human or non-human animal subject when administered in an effective amount to affect the tissue. The bioactive agent may be any class of substance such as a drug molecule or biologic (e.g., polypeptide, carbohydrate, glycoprotein, immunoglobulin, nucleic acid), may be natural products or artificially produced, and may act by any mechanism such as pharmacological, immunological, or metabolic. Examples of classes of bioactive agents include substances that modify the pressure of the eye (e.g., enzyme inhibitors) and anti-angiogenic agents. Some specific examples of bioactive agents include steroids (e.g., corticosteroids), antibiotics, immunosuppressants, immunomodulatory agents, tacrolimus, plasmin activator, anti-plasmin, cyclosporin A, and local anesthetics (e.g., lidocaine). In some embodiments, the bioactive agent is a steroid or antibiotic to treat or prevent eye infection; glaucoma drug such as prostaglandin analog, beta blocker, alpha agonist, or carbonic anhydrase inhibitor; agent for allergy eye relief such as histamine antagonist or non-steroidal anti-inflammatory drug; or mydriatic agent. Unfortunately, in some cases, the bioactive agent or agents included in the fluid may be irritative or damaging to the eye (e.g., cyclosporin A). Advantageously, through its rheological property and other properties, high molecular weight HA in the fluid can alleviate and/or protect the eye from the irritative and/or damaging effects of the biologically active agent or agents within the fluid (i.e., the bioactive agent would be more irritative or more damaging to the eye if administered without the high molecular weight HA).

In some embodiments, the fluid contains no other immunomodulatory agent, immunosuppressive agent, or antibiotic.

In some embodiments, the fluid contains no steroid, antibiotic or immunomodulator. In some embodiments, the fluid contains no other bioactive agent (e.g., no hydrophobic active ingredient).

In some circumstances, it may be desirable to include one or more preservatives or detergents within the fluid. Often, such preservatives and detergents are irritative or damaging to the eye. Advantageously, through its rheological property and other properties, the fluid can alleviate and/or protect the eye from the irritative and/or damaging effects of the preservative or detergent within the fluid. Thus, in some embodiments, the fluid further comprises a preservative or detergent that is irritative or damaging to the eye (i.e., a preservative or detergent that would be more irritative or more damaging to the eye if administered without the high molecular weight HA). In some embodiments, the fluid contains no preservative or detergent.

In some embodiments, the fluid includes cyclosporin A, cetalkoniumchloride, tyloxapol, or a combination of two or more of the foregoing.

In some embodiments, the fluid is administered to the subject before, during, and/or after administration of another composition comprising a bioactive agent to the subject. In some circumstances, it may be desirable to include one or more preservatives or detergents within the other composition. As indicated above, often, such preservatives and detergents are irritative or damaging to the eye, and some bioactive agents themselves may be irritative or damaging to the eye. Advantageously, through its rheological property and other properties, the fluid can alleviate and/or protect the eye from the irritative and/or damaging effects of the bioactive agent, preservative, and/or detergent within the other composition. Thus, the bioactive agent, preservative, and/or detergent within the other composition would be more irritative or more damaging to the eye if administered without the fluid.

In some embodiments, the other composition includes one or more of an antibiotic, immunosuppressant, or immunomodulatory agent.

In some embodiments, the other composition includes cyclosporin A, cetalkoniumchloride, tyloxapol, or a combination of two or more of the foregoing.

The other composition administered to the subject may be in any form and administered by any route (e.g., local or systemic). In some embodiments, the other composition is administered to the eye, e.g., topically, or by intraocular application or injection into ocular tissue. In some embodiments, the other composition is topically administered to the ocular surface.

In some embodiments, the fluid or other composition includes a preservative or detergent, and the preservative or detergent has antibiotic activity. In other embodiments, the preservative or detergent does not have antibiotic activity.

In some embodiments, the preservative or detergent included in the fluid or other composition is a chemical preservative or oxidative preservative.

In some embodiments, the preservative or detergent included in the fluid or other composition is one that kills susceptible microbial cells by disrupting the lipid structure of the microbial cell membrane, thereby increasing microbial cell membrane permeability.

In some embodiments, the preservative or detergent included in the fluid or other composition is one that causes damage to the corneal tissues, such as corneal epithelium, endothelium, stroma, and interfaces such as membranes.

In some embodiments, the preservative or detergent included in the fluid or other composition is selected from the group consisting of quaternary ammonium preservative (e.g., benzalkonium chloride (BAK) or cetalkoniumchloride), chlorobutanol, edetate disodium (EDTA), polyquaternarium-1 (e.g., POLYQUAD™ preservative), stabilized oxidizing agent (e.g., stabilized oxychloro complex (e.g., PURITE™ preservative)), ionic-buffered preservative (e.g., SOFZIA™ preservative), polyhexamethylene biguanide (PHMB), sodium perborate (e.g., GENAQUA™ preservative), tylopaxol, and sorbate.

In some embodiments, the fluid is at least essentially mucin-free; or in other words having a mucin concentration of <0.3% w/v.

In some embodiments, the fluid includes a preservative. In other embodiments, the fluid does not include a preservative (i.e., the fluid is preservative-free).

In some embodiments, the fluid further includes a glycosaminoglycan (GAG), i.e., includes one or more GAGs in addition to the HA; electrolyte (e.g., sodium chloride); buffer (e.g., phosphate buffer); or a combination of two or more of the foregoing.

In some embodiments, the fluid has a pH of 6.8 to 7.6. In some embodiments, the fluid has one or more of the characteristics listed in Table 1. In some embodiments, the fluid has all of the characteristics listed in Table 1.

Another aspect of the invention concerns a kit that may be used for carrying out the method of the invention described herein, i.e., alleviating idiopathic ocular pain. The kit comprises the fluid described herein in a container, and packaging. Suitable containers include, for example, bottles, vials, syringes, blister pack, etc. The containers may be formed from a variety of materials such as glass or plastic.

The kit may include one or more soft or rigid contact lenses for use in conjunction with the fluid. For example, the fluid may be topically administered to the eye before placement of the contact lens on the ocular surface, such that the fluid is entrapped between the contact lens and the ocular surface. The contact lens may be any type or category, such as corneo-scleral lenses, semi-scleral lenses, miniscleral lenses, and full scleral lenses.

The kit may include a delivery agent (separately or in association with the fluid) that is to be brought into contact with the ocular surface or other part of the eye. For example, the kit may include one or more contact lenses or particles (e.g., microparticles or nanopartieles) that are coated with the fluid and/or release the fluid onto the ocular surface.

Optionally, the kit may include a device for dispensing eye drops (e.g., an eye dropper), which may or may not serve as a container for the fluid in the kit before the kit's outer packaging is accessed (e.g., opened), i.e., the eye drop dispensing device may function to contain the fluid provided in the unaccessed (unopened) kit, or may be empty and receive the fluid after the kit is accessed. Optionally, the kit may include a label or packaging insert with printed or digital instructions for use of the kit, e.g., for carrying out the method of the invention.

Kits can include packaging material that is compartmentalized to receive one or more containers such as vials, tubes, and the like, each of the container(s) including one of the separate elements to be used in a method described herein. Packaging materials for use in packaging pharmaceutical products include, by way of example only U.S. Pat. Nos. 5,323,907, 5,052,558 and 5,033,252. Examples of pharmaceutical packaging materials include, but are not limited to, blister packs, bottles, tubes, pumps, bags, vials, light-tight sealed containers, syringes, bottles, and any packaging material suitable for a selected formulation and intended mode of administration and treatment.

A kit may include one or more additional containers, each with one or more of various materials desirable from a commercial and user standpoint for use of the compositions described herein. Non-limiting examples of such materials include, but not limited to, buffers, diluents, carrier, package, container, vial and/or tube labels listing contents and/or instructions for use, and package inserts with instructions for use.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In some embodiments of the kit, the fluid can be presented in a pack or dispenser device which can contain one or more unit dosage forms containing a composition disclosed herein. The pack can for example contain metal or plastic foil, such as a blister pack. The pack or dispenser device can be accompanied by instructions for administration.

Fluid Preparation

In some embodiments, the HA or HA analogue of the fluid has an intrinsic viscosity of greater than 2.5 m$^3$/kg and a concentration of <0.2% w/v. In some embodiments, the hyaluronic acid has an intrinsic viscosity of greater than 2.9 m$^3$/kg.

Viscoelasticity is defined as characteristics of a fluid having both viscous and elastic properties. The zero shear viscosity is determined as the steady shear plateau viscosity at vanishing shear rate. For highly viscous formulations, measurement with a controlled stress rheometer is preferred.

The relation between molecular weight and intrinsic viscosity [η] in m$^3$/kg is given through the Mark-Houwink equation:

$$[\eta] = k \cdot (M_{rm})^a$$

with $M_{rm}$ being the molecular mass in MDa
and the coefficients $$k = 1.3327 \cdot 10^{-4}$$

and $$a = 0.6691$$

which values for k and a having been found as most predictive.

The fluid may be produced by: sterilizing the filling line; adding purified water or water for injection (WFI) to a stainless steel mixing tank; adding salts while mixing; slowly adding HA and mixing until a homogeneous solution/fluid is achieved; adjusting pH value by adding NaOH or HCl, if required, while continuing the mixing process; transferring the solution over a 1 μm pore size filter cartridge to a sterile holding tank; and aseptically filling the solution via sterile filtration into the sterile primary package (monodose or vial). In the case of monodoses, this may be done by a blow-fill-seal (BFS) process.

Preferably, the fluid is at least essentially mucin-free or in other words having a mucin concentration of <0.3% w/v. This means that the flow behavior or properties essentially is reached or adjusted by hyaluronan and not by mucin naturally present in the subject's tear fluid and mainly responsible for the flow behavior thereof.

It is preferred that if substances are added that increase the viscosity, they are added towards, or during, or as a final step. The mixing is carried out so as to reach a homogeneous mixture. As an alternative or in addition, it is preferred to initially provide purified water or water for injection as a basis, and then, optionally, electrolytes, buffers and substances which do not increase the viscosity are added at first to the purified water or water for injection.

HA is further described in the monograph of the European Pharmacopoeia 9.0, page 3583 (Sodium Hyaluronate), which is incorporated herein by reference in its entirety.

In some embodiments, the fluid used in the method and kit of the invention has one or more of the characteristics listed in Table 1. In some embodiments, the fluid used in the method and kit of the invention has all of the characteristics listed in Table 1.

TABLE 1

| Characteristic | Specification | Test Method |
| --- | --- | --- |
| Appearance | clear and colorless solution, free from visible impurities | Ph.Eur. |
| pH value | 6.8-7.6 | Ph.Eur. |
| Osmolality | 240-330 mosmol/kg | Ph.Eur. |
| HA concentration | 0.10-0.19% w/v | Ph.Eur. |
| NaCl concentration | 7.6-10.5 g/l | Ph.Eur. |
| Sterility | Sterile | Ph.Eur. |
| Phosphate concentration | 1.0-1.4 mmol/l | Ph.Eur. |

Fluid Testing

Fluids may be evaluated for their effects in vivo by administering fluids of a selected molecular weight and selected concentration of HA or HA analogue as eye drops to animals (such as rats) with healthy eyes, and to animals in which the main lacrimal glands have been removed. Nerve responses may be recorded using electrodes implanted into the ganglion of the animals.

Definitions

The term "a," "an," "the" and similar terms used in the context of the present invention (especially in the context of the claims) are to be construed to cover both the singular and plural unless otherwise indicated herein or clearly contradicted by the context. Thus, for example, reference "a cell" or "a compound" should be construed to cover both a singular cell or singular compound and a plurality of cells and a plurality of compounds unless indicated otherwise or clearly contradicted by the context. Similarly, the word "or" is intended to include "and" unless the context clearly indicates otherwise. The abbreviation, "e g." is derived from the Latin exempli gratia, and is used herein to indicate a non-limiting example. Thus, the abbreviation "e." is synonymous with the term "for example."

The term "effective amount" in the context of the administered fluid of the invention means the amount of fluid necessary to obtain a desired result, such as alleviation (reduction or elimination) of ocular pain.

As used herein, the term "homeostasis" refers to the capacity of a physiological system to maintain internal stability, or to the state of stability itself, owing to the coordinated response of its parts to any situation or stimulus that would tend to disturb its normal, non-pathological condition or function.

As used herein, the term "hyaluronic acid" (HA) refers to the glycosaminoglycan composed of disaccharide repeats of N-acetylglucosamine and glucuronic acid found in nature, also known as hyaluronan (e.g., the straight chain, glycosaminoglycan polymer composed of repeating units of the disaccharide [-D-glucuronic acid-b1,3-N-acetyl-D-glucosamine-b1,4-]n), as well as derivatives of hyaluronan having chemical modifications such as esters of hyaluronan, amide derivatives, alkyl-amine derivatives, low molecular weight and high molecular weight forms of hyaluronans, and cross-linked forms. Thus, the disaccharide chain may be linear or non-linear. Hyaluronan can be cross-linked by attaching cross-linkers such as thiols, methacrylates, hexadecylamides, and tyramines (Cowman M K et al., Carbohydrate Polymers 2000, 41:229-235; Takigami S et al., Carbohydrate Polymers, 1993, 22:153-160; Koehler L et al., *Scientific Reports*, 2017, 7, article no. 1210; and Pavan M et al., *Carbohydr Polym*, 2013, 97(2): 321-326; which are each incorporated herein by reference in their entirety).

The term "hyaluronic acid" or HA includes HA itself and pharmaceutically acceptable salts thereof. The HA can be formulated into pharmaceutically-acceptable salt forms. Pharmaceutically-acceptable salts of HA can be prepared using conventional techniques.

The term "high molecular weight" or "HMW" in the context of hyaluronic acid or a hyaluronic acid analogue of the invention refers to hyaluronic acid or hyaluronic acid analogue having an intrinsic viscosity of >2.5 m$^3$/kg as determined by the method of the European Pharmacopoeia 9.0, "Sodium Hyaluronate", page 3584 (which is incorporated herein by reference in its entirety). Briefly, the intrinsic viscosity [η] is calculated by linear least-squares regression analysis using the Martin equation: $\text{Log}_{10}$ $(n_r-1/c)=\text{Log}_{10}$ [η]+κ[η]c. In some embodiments, the high molecular weight hyaluronic acid or analogue has an intrinsic viscosity of greater than 2.9 m$^3$/kg.

As used herein, the term "immunocompromised" refers to a subject with an innate, acquired, or induced inability to develop a normal immune response. An immunocompromised subject, therefore, has a weakened or impaired immune system relative to one of a normal subject. A subject with a weakened or impaired immune system has an "immunodeficiency" or "immunocompromised condition," which is associated with a primary or secondary deficiency, induced or non-induced, in one or more of the elements of the normal immune defense system. An immunocompromised condition may be due to a medical treatment, e.g., radiation therapy, chemotherapy or other immunosuppressing treatment, such as induced by treatment with steroids, cyclophosphamide, azathioprine, methotrexate, cyclosporine or rapamycin, in particular in relation to cancer treatment or the treatment or prevention of transplant rejection. The presence of an immunocompromised condition in a subject can be diagnosed by any suitable technique known to persons of skill the art. A strong indicators that an immunocompromised condition may be present is when rare diseases occur or the subject gets ill from organisms that do not normally cause diseases, especially if the subject gets repeatedly infected. Other possibilities are typically considered, such as recently acquired infections, for example, HIV, hepatitis, tuberculosis, etc. Generally, however, definitive diagnoses are based on laboratory tests that determine the exact nature of the immunocompromised condition. Most tests are performed on blood samples. Blood contains antibodies, lymphocytes, phagocytes, and complement components, all of the major immune components that might cause immunodeficiency. A blood cell count can be used to determine if the number of phagocytic cells or lymphocytes is below normal. Lower than normal counts of either of these two cell types correlates with an immunocompromised condition. The blood cells are also typically checked for their appearance. Sometimes, a subject may have normal cell counts, but the cells are structurally defective. If the lymphocyte cell count is low, further testing is usually conducted to determine whether any particular type of lymphocyte is lower than normal. A lymphocyte proliferation test may be conducted to determine if the lymphocytes can respond to stimuli. The failure to respond to stimulants correlates with an immunocompromised condition. Antibody levels and complement levels can also be determined for diagnosing the presence of an immunocompromised condition.

The term "isolated," when used as a modifier of a composition, means that the compositions are made by human intervention or are separated from their naturally occurring in vivo environment. Generally, compositions so separated are substantially free of one or more materials with which they normally associate with in nature, for example, one or more protein, nucleic acid, lipid, carbohydrate, cell membrane. A "substantially pure" molecule can be combined with one or more other molecules. Thus, the term "substantially pure" does not exclude combinations of compositions. Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (for nucleic acid and peptide).

As used herein, the term "ocular pain" (ophthalmalgia) refers to an unpleasant sensation in, on, or around the eye. The pain in the eye may be described, for example, as a burning, throbbing, aching, itching, tiring-exhausting, sharp, tender, throbbing, heavy, stabbing, gnawing, sickening, splitting, punishing-cruel, fearful, shooting, or cramping sensation in or around the eye. It may also feel like the subject has a foreign object in the eye. In some embodiments, the ocular pain is experienced by the subject as (a) one or both eyes that feel gritty, or (b) one or both eyes that feel pain or sore, or both (a) and (b). The ocular pain may be perceived at the ocular surface and/or other parts of the eye. The ocular pain may be periodic/episodic, or constant. Ocular pain may be caused by any type of stimulus or combination of stimuli (mechanical, chemical, thermal (heat or cold)). As used herein, the term "idiopathic ocular pain" refers to ocular pain having an unknown cause.

As used herein, the phrase "detectable signs known to cause ocular pain" means signs of ocular surface damage, such as erosions and cysts, known to cause pain, irritation, and discomfort. Signs known to cause ocular pain may be detected, for example, by fluorescein staining, lissamine green staining, rose Bengal staining, and other vital staining that allows visualization of epithelial disruption and other pathophysiologic changes to tissues in their living state.

As used herein, the term "ocular surface" refers to the cornea and conjunctiva, and portions thereof, including the conjunctiva covering the upper and lower lids. The fluid may be topically administered to one or more parts of the ocular surface, including, for example, the entire ocular surface.

As used herein, the term "pain receptor" refers to any of the many nerve endings that normally function to warn of potentially harmful changes in the environment, such as excessive pressure or temperature. For example, the receptor may be a thermal, mechanical, chemical, sleeping/silent, or polymodal nociceptor, and may be connected to a variety of nerve fibers, such as A-alpha, A-beta, A-delta, and C-nerve fibers. Each sensory receptor fiber class evokes qualitatively distinct sensations and evokes distinct autonomic reflex responses. For example, mechano-, polymodal, and cold corneal receptors evoke qualitatively distinct unpleasant sensations; cold thermoreceptors regulate basal tear secretion; and mechano- and polymodal nociceptors evoke irritation-induced reflex tearing and blinking.

"Pharmaceutically acceptable salt" includes both acid and base addition salts. A pharmaceutically acceptable salt of HA or any one of the other compounds described herein is intended to encompass any and all pharmaceutically suitable salt forms. Preferred pharmaceutically acceptable salts described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra. In some embodiments, the pharmaceutically acceptable salt is sodium salt (see "Sodium Hyaluronate" at page 3583 of European Pharmacopoeia 9.0, which is incorporated herein by reference).

As used herein, the terms "subject", "patient", and "individual" refer to a human or non-human animal capable of having ocular pain. A subject also refers to, for example, primates (e.g., humans), cows, sheep, goats, horses, dogs, cats, rabbits, rats, mice, fish, birds and the like. In some embodiments, the subject is a mammal. In some embodiments, the subject is a human. Thus, the methods may be carried out in the medical setting and the veterinary setting. The non-human animal subject may be, for example, a pet or an animal model of an ocular or non-ocular disease.

In some embodiments, the subject is immunocompromised, i.e., is in an immunocompromised condition.

The phrase "topical administration" is used herein in its conventional sense to mean topical delivery to the desired anatomical site, such as the ocular surface. In some embodiments, drops of the fluid are topically administered to the ocular surface in an amount and frequency as needed to alleviate ocular pain. The fluid comprising hyaluronic acid or hyaluronic acid analogue may be applied directly or indirectly to the ocular surface by any manner that allows an effective amount of the fluid and ocular surface to make contact. For example, the fluid may be applied directly to the ocular surface, such as via eye drops or lavage, or applied indirectly via a delivery agent (i.e., a fluid delivery agent) that is brought into contact with the ocular surface or other part of the eye. Optionally, the fluid may be topically administered to the ocular surface in conjunction with a soft or rigid contact lens. For example, the fluid may be topically administered before placement of the contact lens on the ocular surface, such that the fluid is entrapped between the contact lens and the ocular surface. The contact lens may be any type or category, such as corneo-scleral lenses, semi-scleral lenses, miniscleral lenses, and full scleral lenses.

An example of a delivery agent is a contact lens or particle (e.g., microparticles or nanoparticles) that is coated with the fluid and/or releases the fluid onto the ocular surface. Such delivery agents may be composed of various materials, such as natural or synthetic polymers. In some embodiments, the delivery agent may itself be administered as drops.

Exemplified Embodiments

Embodiment 1. A method for relieving idiopathic ocular pain, comprising administering an effective amount of a fluid comprising hyaluronic acid, a hyaluronic acid analogue, or a combination thereof, to the eye of a human or non-human animal subject, wherein the fluid is administered after onset of the idiopathic ocular pain and in the absence of detectable signs known to cause ocular pain.

Embodiment 2. The method of embodiment 1, wherein the fluid contains no other bioactive agent (e.g., no hydrophobic active ingredient).

Embodiment 3. The method of embodiment 1 or 2, wherein the fluid contains no other immunomodulatory agent, immunosuppressive agent, or antibiotic.

Embodiment 4. The method of embodiment 1 or 3, wherein the fluid further comprises a bioactive agent (e.g., a hydrophobic active ingredient).

Embodiment 5. The method of any one of embodiments 1 to 3, wherein the fluid further comprises a preservative or detergent.

Embodiment 6. The method of any one of embodiments 1 to 4, wherein the fluid does not further comprise a preservative (i.e., the fluid is preservative-free).

Embodiment 7. The method of any preceding embodiment, wherein the fluid is administered before, during, and/or after administration of a composition comprising: a bioactive agent (e.g., a hydrophobic active ingredient), preservative, detergent, or combination of two or more of the foregoing.

Embodiment 8. The method of any preceding embodiment, wherein the fluid is topically administered to the ocular surface.

Embodiment 9. The method of any preceding embodiment, wherein the fluid is topically administered directly to the ocular surface as drops or as a wash (e.g., lavage).

Embodiment 10. The method of embodiment 9, wherein drops of the fluid are topically administered to the ocular surface in an amount and frequency as needed to alleviate ocular pain.

Embodiment 11. The method of embodiment 10, wherein 1 to 3 drops are topically administered, 1 to 20 times per day.

Embodiment 12. The method of any one of embodiments 8 to 11, wherein the fluid is topically administered in conjunction with a soft or rigid contact lens, wherein the contact lens is placed on the ocular surface after topical administration of the fluid, entrapping the fluid between the contact lens and the ocular surface.

Embodiment 13. The method of any one of embodiments 1 to 7, wherein the fluid is administered indirectly to the eye by a delivery agent (a fluid delivery agent) that is administered to the eye (e.g., a contact lens or particle that is coated with and/or secretes the fluid on to the ocular surface).

Embodiment 14. The method of any one of embodiments 1 to 7 or 13, wherein the fluid is administered by intra-ocular application or by injection into ocular tissue.

Embodiment 15. The method of any preceding embodiment, wherein the fluid continues to be administered for a time after relief of the idiopathic pain is achieved.

Embodiment 16. The method of any preceding embodiment, wherein the fluid further comprises an additional glycosaminoglycan (GAG), an electrolyte (e.g., sodium chloride), a buffer (e.g., phosphate buffer), or a combination of two or more of the foregoing.

Embodiment 17. The method of any preceding embodiment, wherein the fluid comprises high molecular weight hyaluronic acid and/or high molecular weight hyaluronic acid analogue.

Embodiment 18. The method of embodiment 17, wherein the fluid comprises high molecular weight hyaluronic acid and/or high molecular weight hyaluronic acid analogue having an intrinsic viscosity of >2.5 m$^3$/kg and a concentration of <0.2% w/v.

Embodiment 19. The method of embodiment 17 or 18, wherein the high molecular weight hyaluronic acid and/or high molecular weight hyaluronic acid analogue has an intrinsic viscosity of >2.9 m$^3$/kg.

Embodiment 20. The method of any preceding embodiment, wherein the hyaluronic acid and/or hyaluronic acid analogue has a molecular weight of at least 3 million Daltons.

Embodiment 21. The method of any preceding embodiment, wherein the hyaluronic acid and/or hyaluronic acid analogue has a molecular weight in the range of 3 million to 4 million Daltons.

Embodiment 22. The method of any preceding embodiment, wherein the fluid comprises high molecular weight hyaluronic acid and/or high molecular weight hyaluronic acid analogue having a concentration of 0.10 to 0.19% w/v.

Embodiment 23. The method of any preceding embodiment, wherein the fluid has a pH of 6.8 to 7.6.

Embodiment 24. The method of any preceding embodiment, wherein the fluid has one or more of the characteristics of the fluid in Table 1.

Embodiment 25. The method of any preceding embodiment, wherein the ocular pain is experienced by the subject as (a) one or both eyes that feel gritty, or (b) one or both eyes that feel pain or sore, or both (a) and (b).

Embodiment 26. The method of any preceding embodiment, wherein the subject is human.

The invention is described only exemplarily by the embodiments in the description and drawings and is not limited thereto but rather includes all variations, modifications, substitutions, and combinations the expert may take from the complete documents of this application under consideration of and/or combination with his specific knowledge.

All patents, patent applications, provisional applications, and publications referred to or cited herein are incorporated by reference in their entirety, including all figures and tables, to the extent they are not inconsistent with the explicit teachings of this specification.

All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for relieving idiopathic ocular pain, comprising topically administering an effective amount of a fluid comprising hyaluronic acid having an intrinsic viscosity of >2.5 m$^3$/kg and a concentration of <0.2% w/v to the eye of a human or non-human animal subject, wherein the fluid is administered after onset of the idiopathic ocular pain and in the absence of detectable signs known to cause ocular pain.

2. The method of claim 1, wherein the fluid contains no other bioactive agent.

3. The method of claim 1, wherein the fluid includes no other immunomodulatory agent, immunosuppressive agent, or antibiotic.

4. The method of claim 1, wherein the fluid further comprises a bioactive agent.

5. The method of claim 1, wherein the fluid further comprises a preservative or detergent.

6. The method of claim 1, wherein the fluid does not further comprise a preservative.

7. The method of claim 1, wherein the fluid is administered before, during, and/or after administration of a composition comprising: a bioactive agent, preservative, detergent, or combination of two or more of the foregoing.

8. The method of claim 1, wherein the fluid is topically administered directly to the ocular surface as drops or as a wash.

9. The method of claim 8, wherein drops of the fluid are topically administered to the ocular surface in an amount and frequency as needed to alleviate ocular pain.

10. The method of claim 1, wherein the fluid is topically administered in conjunction with a soft or rigid contact lens, wherein the contact lens is placed on the ocular surface after topical administration of the fluid, entrapping the fluid between the contact lens and the ocular surface.

11. The method of claim 1, wherein the fluid further comprises an additional glycosaminoglycan (GAG), an electrolyte, a buffer, or a combination of two or more of the foregoing.

12. The method of claim 1, wherein the hyaluronic acid has an intrinsic viscosity of >2.9 m$^3$/kg.

13. The method of claim 1, wherein the hyaluronic acid has a molecular weight of at least 3 million Daltons.

14. The method of claim 1, wherein the fluid comprises high molecular weight hyaluronic acid having a concentration of 0.10 to 0.19% w/v.

15. The method of claim 1, wherein the ocular pain is experienced by the subject as (a) one or both eyes that feel gritty, or (b) one or both eyes that feel pain or sore, or both (a) and (b).

16. The method of claim 1, wherein the subject is human.

* * * * *